US00PP11920P2

(12) United States Plant Patent
Glicenstein

(10) Patent No.: US PP11,920 P2
(45) Date of Patent: Jun. 12, 2001

(54) AZALEA PLANT NAMED 'PROMISE'

(75) Inventor: Leon Glicenstein, Lebanon, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/498,710

(22) Filed: Feb. 7, 2000

(51) Int. Cl.[7] ..... A01H 5/00
(52) U.S. Cl. ..... Plt./239
(58) Field of Search ..... Plt./238, 239, 240

(56) References Cited

PUBLICATIONS

David G. Leach, Rhododendrons of the World and How to Grow Them, pp. 427 and 441, 1961.*

* cited by examiner

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Azalea plant named 'Promise', characterized by its shiny dark green leaves that do not abscise during the cooling and forcing periods; dense, uniform and outwardly spreading plant habit; freely branching habit; rapid flowering after forcing; numerous large coral-colored flowers with smooth petal margins; double flower form; excellent postproduction longevity with plants maintaining good flower substance for more than four weeks in an interior environment; and very low incidence of infection with Cylindrocladium in inoculated trials.

1 Drawing Sheet

BACKGROUND OF THE INVENTION

The present Invention relates to a new and distinct cultivar of Azalea, botanically known as *Rhododendron hybrida*, an evergreen greenhouse-forcing type Azalea, and hereinafter referred to by the name 'Promise'.

The new Azalea is a product of a planned breeding program conducted by the Inventor in Alva, Fla. The objective of the breeding program is to create new Azalea varieties having uniform plant habit and uniform flowering, numerous flowers, dark green foliage, good foliage retention during the cooling and forcing periods, resistance to Cylindrocladium, and excellent postproduction longevity.

The new Azalea originated from a cross made by the Inventor in Alva, Fla., of a proprietary selection identified as code number YB-0334 as the female, or seed, parent with a propriety selection identified as code number YB-0815 as the male, or pollen, parent.

Compared to plants of the female parent, plants of the new Azalea are more vigorous; have a more uniform plant habit; have better foliage retention and better tolerance to the cooling treatment. Compared to plants of the male parent, plants of the new Azalea are more outwardly spreading and have larger leaves and flowers.

The new Azalea was discovered and selected by the Inventor as a flowering plant within the progeny of the stated cross in a controlled environment in Alva, Fla., in March, 1994. The selection of this plant was based on its desirable flower color, profuse and uniform flowering, improved foliage retention, uniform plant habit, excellent postproduction longevity, and resistance to Cylindrocladium.

Asexual reproduction of the new Azalea by terminal cuttings taken in a controlled environment in Alva, Fla., has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, nutrition and water status without, however, any variance in genotype.

The following traits have been repeatedly observed and are determined to be the unique characteristics of 'Promise'. These characteristics in combination distinguish 'Promise' as a new and distinct cultivar:

1. Shiny dark green leaves that do not abscise during the cooling and forcing periods.
2. Dense, uniform and outwardly spreading plant habit.
3. Very freely branching.
4. Rapid flowering after forcing.
5. Numerous large coral-colored flowers with smooth petal margins.
6. Double flower form.
7. Flowers that do not shatter.
8. Good flower color retention even under high light.
9. Excellent postproduction longevity with plants maintaining good flower substance for more than four weeks in an interior environment.
10. Very low incidence of infection with Cylindrocladium in inoculated trials.

Plants of the new Azalea can be compared to plants of the cultivar 'Champagne', disclosed in U.S. Plant Pat. No. 9,131. However, in side-by-side comparisons conducted in Alva, Fla., plants of the new Azalea differ from plants of the cultivar 'Champagne' in the following characteristics:

1. After cooling, plants of the new Azalea flower about five to six days earlier than plants of the cultivar 'Champagne'.

2. Flower form of plants of the new Azalea is double whereas flower form of plants of the cultivar 'Champagne' is semi-double hose-in-hose.

3. Petal margin of plants of the new Azalea is smooth whereas petal margin of plants of the cultivar 'Champagne' is ruffled.

4. Plant habit of plants of the new Azalea is more uniform and more outwardly spreading than the plant habit of plants of the cultivar 'Champagne' which tends to be upright and somewhat tiered.

5. Leaves of plants of the new Azalea are not susceptible to amide injury (foliar burn) whereas leaves of plants of the cultivar 'Champagne' are susceptible to amide injury.

6. Flowering plants of the new Azalea last about five days longer than flowering plants of the cultivar 'Champagne' in postproduction longevity trials.

Plants of the new Azalea can also be compared to plants of the cultivar 'Cherish', disclosed in U.S. Plant Pat. No. 9,910. However, in side-by-side comparisons conducted in Alva, Fla., plants of the new Azalea differ from plants of the cultivar 'Cherish' in the following characteristics:

1. After cooling, plants of the new Azalea flower about 10 to 12 days earlier than plants of the cultivar 'Cherish'.

2. Plants of the new Azalea have a less uniform, but more outwardly spreading plant habit than plants of the cultivar 'Cherish'.

3. Flower form of plants of the new Azalea is double whereas flower form of plants of the cultivar 'Cherish' is semi-double hose-in-hose.

4. Flower color of plants of the new Azalea is more uniform and slightly lighter than flower color of plants of the cultivar 'Cherish'.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the actual colors of the new Azalea.

The photograph at the top of the sheet comprises a top perspective view of a typical plant of 'Coral Reef'.

The photograph at the bottom of the sheet is a close-up view of typical flowers of 'Coral Reef'.

DETAILED BOTANICAL DESCRIPTION

The aforementioned and following observations, measurements, values, and comparisons describe plants grown in Alva, Fla., in 12.5-cm containers with day temperatures ranging from 16 to 35° C. and night temperatures ranging from 10 to 24° C. Plants were grown under 50 percent polypropylene shade cloth reducing ambient light levels to about 4,000 to 5,000 footcandles. Plants used for the description and photographs were about 12 months from planting. After flower bud development, plants were cooled at 3 to 5° C. for six weeks to break flower bud dormancy. Plants were subsequently forced into flower under commercial conditions in a polyethylene-covered greenhouse. In the following description, color references are made to The Royal Horticultural Society Colour Chart except where general terms of ordinary dictionary significance are used.

Botanical classification:

*Botanical.*—*Rhododendron hybrida* 'Promise'.

*Commercial.*—Evergreen greenhouse-forcing type Azalea.

Parentage:

*Female or seed parent.*—Proprietary selection of *Rhododendron hybrida* identified as code number YB-0334.

*Male or pollen parent.*—Proprietary selection of *Rhododendron hybrida* identified as code number YB-0815.

Propagation:

*Type.*—By terminal cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Vigorous; finely-branched.

Plant description:

*Plant form and growth habit.*—Perennial, evergreen; outwardly spreading, inverted triangle, uniform and symmetrical plant habit; moderately vigorous growth habit. Freely flowering; numerous flowers per plant.

*Branching habit.*—Very freely branching; about five lateral branches develop after removal of terminal apex.

*Plant height, soil level to top of flowers.*—About 25 cm.

*Plant diameter, area of spread.*—About 47 cm.

*Lateral branch description.*—Length: About 22 cm. Diameter at base: About 5.5 mm. Color: Immature: Between 144A and 144B. Mature: Woody, between 165A and 165B. Texture: Sparsely pubescent.

Foliage description:

*Arrangement.*—Alternate, single.

*Length.*—About 4.4 cm.

*Width.*—About 1.8 cm.

*Shape.*—Elliptic.

*Apex.*—Mucronate.

*Base.*—Attenuate.

*Margin.*—Entire.

*Texture.*—Leathery, pubescent on both surfaces.

*Color.*—Young foliage, upper surface: Shiny; 147A. Young foliage, lower surface: Close to 147B. Mature foliage, upper surface: Shiny; much darker than 147A. Mature foliage, lower surface: Close to 147B.

*Petiole.*—Length: About 7.5 mm. Diameter: About 2 mm. Color: Close to 147B.

Flower description:

*Natural flowering season.*—Spring after sufficient cool period.

*Flower arrangement.*—Flowers arranged singly at terminals with usually about three flowers per apex. Flowers face upward and outward. Very freely flowering. Not fragrant.

*Flower appearance.*—Large-sized star-shaped double flower form. Coral-colored petals. Flowers persistent.

*Flower diameter.*—About 9.1 cm.

*Flower depth.*—About 4.4 cm.

*Postproduction longevity.*—Under interior conditions, plants maintain good flower substance for more than four weeks.

*Flower bud* (*just starting to show petal color*).—Rate of opening: About three to four days depending on temperatures. Length: About 1.9 cm. Diameter: About 8 mm. Shape: Ovoid, elongated. Color: 51A.

*Petals.*—Arrangement: Double flower form fused at base; two whorls of petals; about 8–10. Length, outer petals: About 5.75 cm. Width, other petals: About 4.2 cm. Shape: Elliptic with broadly acute apex. Margin: Entire; mostly smooth. Texture: Smooth, velvety. Color: When opening, upper surface: 51A to 51B. When opening, lower surface: 51A to 51 B. Fully opened, upper surface: 51A to 51B; fading to 51C to 51D. Fully opened, lower surface: 51A to 51B to 51C. Throat: 51C to 51D to white.

*Sepals.*—Arrangement: Five small sepals fused into a star-shaped calyx. Length: About 6 mm. Width: About 4 mm. Shape; Ovate with acute apex. Margin: Entire. Texture: Upper surface, smooth; lower surface and margin, pubescent. Color: Upper surface: 144A to 144B. Lower surface: 144A.

*Peduncles.*—Length: About 1.5 cm. Diameter: About 2 mm. Angle: Upright. Strength: Flexible, but strong. Texture: Pubescent. Color: 144A to 144B.

*Reproductive organs.*—Androecium: Stamens: Most are transformed into petals; if any, typically only one or two free stamens. Anther shape: Oblong. Anther size: About 2 mm by 1 mm. Anther color: Dark purple, close to 79A. Amount of pollen: None observed. Gynoecium: Pistil number: One. Pistil Length: About 7.5 cm. Stigma shape: Rounded. Stigma color: Close to 144B. Style length: About 5.5 mm. Style color: Close to 144B to 144C. Ovary color: 144A; heavily whiskered.

Disease resistance: Very low incidence of infection by Cylindrocladium in inoculated trials; trials repeated in Alva, Fla., during the summers of 1997, 1998 and 1999.

Seed production: Seed production has not been observed.

It is claimed:

1. A new and distinct Azalea plant named ‘Promise’, as illustrated and described.

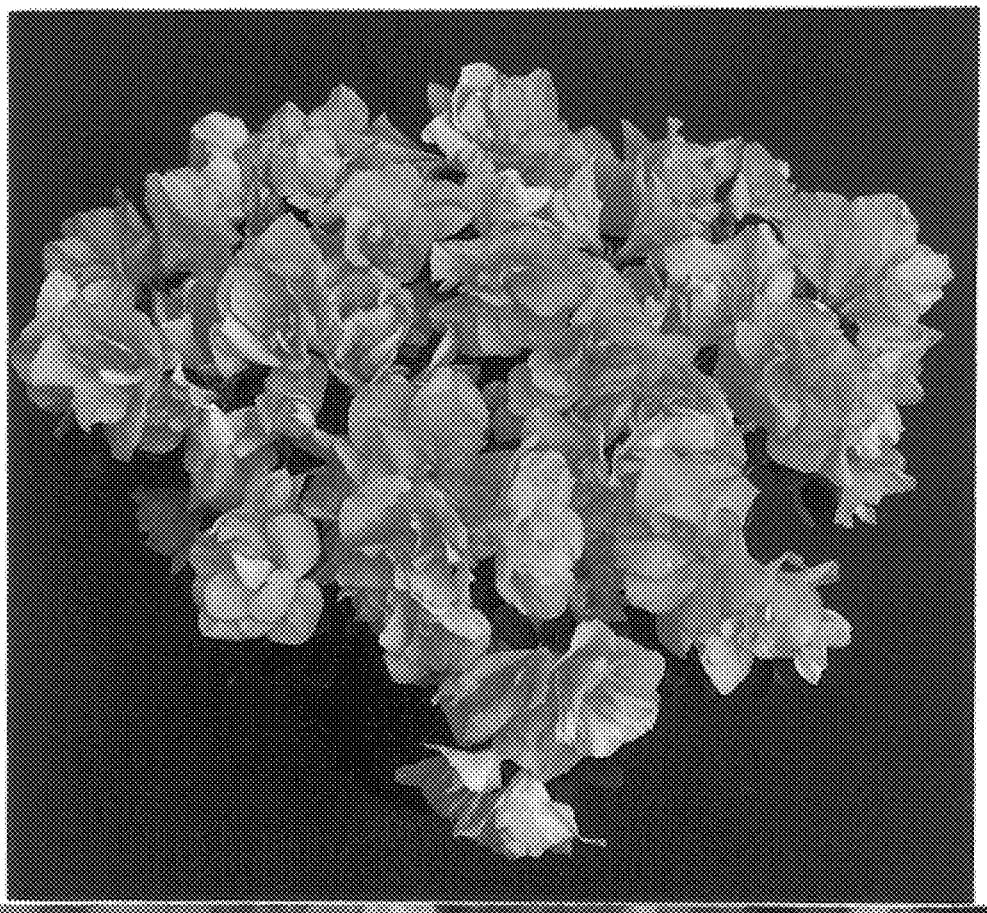
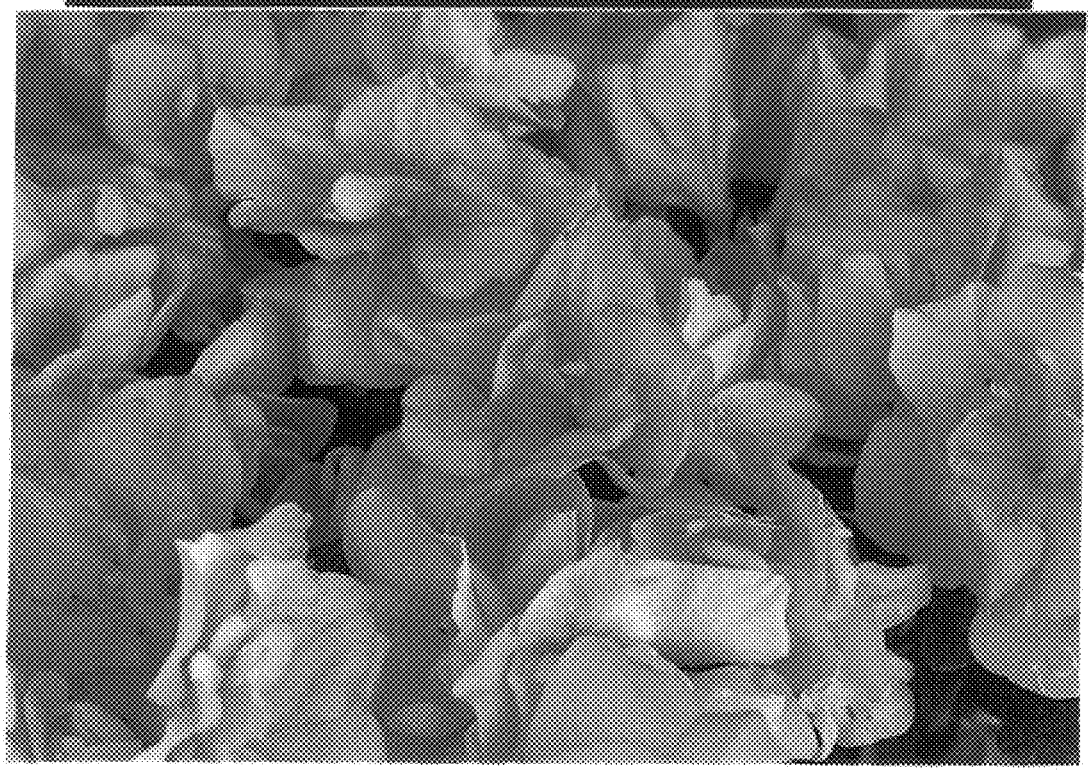

* * * * *